(12) United States Patent
Fujii

(10) Patent No.: US 11,045,216 B2
(45) Date of Patent: Jun. 29, 2021

(54) ROTATING MECHANISM FOR TREATMENT TOOLS

(71) Applicant: Olympus Corporation, Hachioji (JP)

(72) Inventor: Masahiro Fujii, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 351 days.

(21) Appl. No.: 16/353,683

(22) Filed: Mar. 14, 2019

(65) Prior Publication Data
US 2019/0209192 A1    Jul. 11, 2019

Related U.S. Application Data

(63) Continuation of application No. PCT/JP2016/080194, filed on Oct. 12, 2016.

(51) Int. Cl.
*A61B 17/29* (2006.01)
*A61B 17/28* (2006.01)
*A61B 17/00* (2006.01)

(52) U.S. Cl.
CPC .............. *A61B 17/29* (2013.01); *A61B 17/28* (2013.01); *A61B 2017/00367* (2013.01);
(Continued)

(58) Field of Classification Search
CPC . A61B 17/29; A61B 17/28; A61B 2017/2929; A61B 2017/2927;
(Continued)

(56) References Cited

U.S. PATENT DOCUMENTS 6,280,458 B1 * 8/2001 Boche ................. A61B 17/062
606/206
6,569,105 B1 * 5/2003 Kortenbach ........... A61B 10/06
600/562

(Continued)

FOREIGN PATENT DOCUMENTS

CN        102871723 A1    1/2013
JP        2004-016309     1/2004
(Continued)

OTHER PUBLICATIONS

International Search Report and Written Opinion from corresponding International Application No. PCT/JP2016/080194, dated Dec. 13, 2016.

*Primary Examiner* — Katrina M Stransky
(74) *Attorney, Agent, or Firm* — Scully, Scott, Murphy & Presser, P.C.

(57) ABSTRACT

The disclosed technology is directed to a rotating mechanism for a treatment tool or grasping forceps which comprises a rotating member having respective first and second ends. The first end is supported on a distal end of an elongated member for rotation about a longitudinal axis of the elongated member. The grasping forceps is attached to the second end of the rotating member. An axial force transmitting member is configured to be disposed along the elongated member for transmitting axial forces. An actuating member is attached to a distal end of the axial force transmitting member. A converting mechanism is used for converting the linear movement to the rotary movement of the actuating member along the longitudinal axis. The linear movement of the actuating member is not transmitted to the rotating member and the rotary movement of the actuating member about the longitudinal axis is transmitted to the rotating member.

18 Claims, 8 Drawing Sheets

(52) U.S. Cl.
CPC ............... *A61B 2017/00862* (2013.01); *A61B 2017/293* (2013.01); *A61B 2017/2903* (2013.01)

(58) Field of Classification Search
CPC ...... A61B 2017/2903; A61B 2017/293; A61B 2017/2936; A61B 2017/2934; A61B 2017/2933; A61B 2017/00367; A61B 2017/2905; A61B 2017/292; A61B 2017/2923; A61B 2017/2925; A61B 2017/2943; A61B 2017/2946; A61B 2017/2902; A61B 1/00087
See application file for complete search history.

(56) References Cited

U.S. PATENT DOCUMENTS

| | | | | |
|---|---|---|---|---|
| 2010/0087818 | A1* | 4/2010 | Cunningham | A61B 18/1445 606/53 |
| 2011/0071564 | A1* | 3/2011 | Suzuki | A61B 17/29 606/205 |
| 2012/0158043 | A1* | 6/2012 | Suzuki | A61B 17/29 606/205 |
| 2013/0012986 | A1* | 1/2013 | Suzuki | A61B 18/1445 606/208 |
| 2013/0289616 | A1* | 10/2013 | Suzuki | A61B 17/00234 606/205 |
| 2013/0289617 | A1* | 10/2013 | Suzuki | A61B 17/29 606/205 |
| 2015/0032151 | A1* | 1/2015 | Ishida | A61B 17/2909 606/205 |
| 2017/0150950 | A1* | 6/2017 | Thouement | A61B 17/00 |
| 2018/0112422 | A1* | 4/2018 | Fujii | B65B 13/285 |

FOREIGN PATENT DOCUMENTS

| | | |
|---|---|---|
| JP | 2005-237498 | 9/2005 |
| JP | 2008-006159 | 1/2008 |
| JP | 2010-505519 | 2/2010 |
| JP | 2012-200415 | 10/2012 |
| WO | 2008045333 | 4/2008 |
| WO | 2008045353 | 4/2008 |
| WO | 2008045355 | 4/2008 |
| WO | 2008045361 | 4/2008 |
| WO | 2008045367 | 4/2008 |
| WO | 2008045376 | 4/2008 |
| WO | 2008045385 | 4/2008 |
| WO | 2008045386 | 4/2008 |
| WO | 2008045394 | 4/2008 |

* cited by examiner

FIG. 7
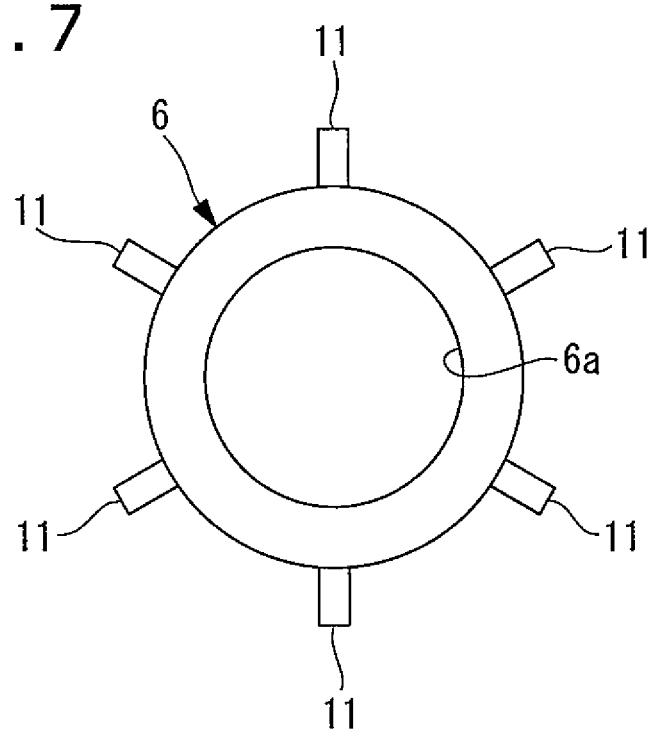
FIG. 8 DISTAL-END SIDE
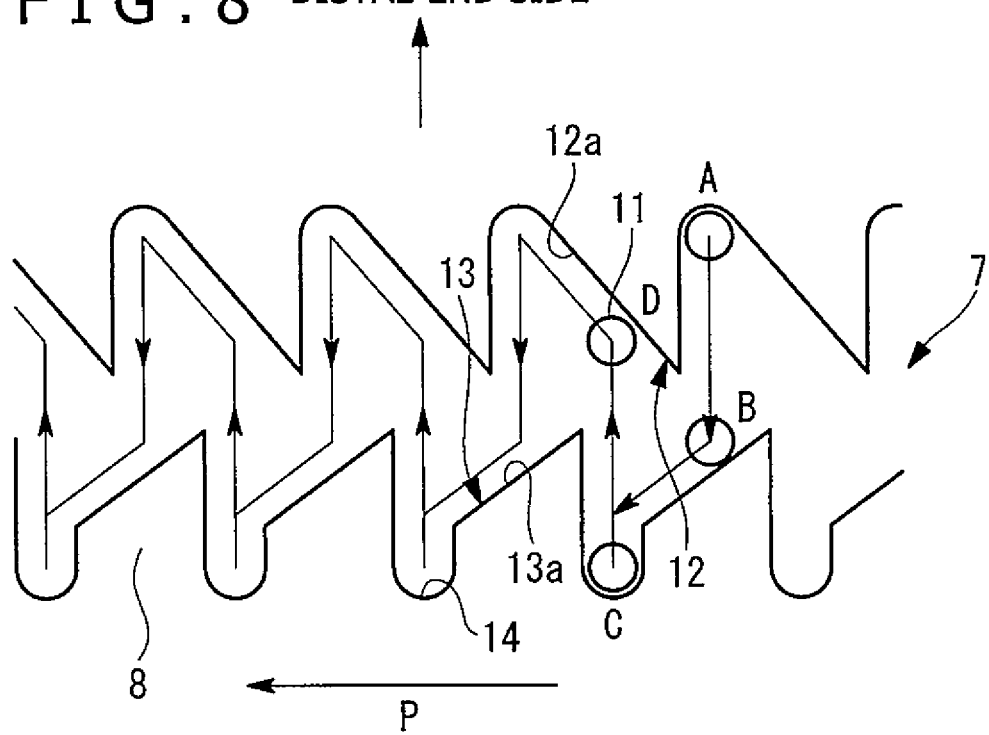

ROTATING MECHANISM FOR TREATMENT TOOLS

CROSS-REFERENCE TO RELATED APPLICATION

This application is a continuation application of PCT Application No. PCT/JP2016/080194 filed on Oct. 12, 2016, which is hereby incorporated by reference in its entirety.

TECHNICAL FIELD

The disclosed technology relates to a rotating mechanism for treatment tools.

DESCRIPTION OF THE RELATED ART

There is known a rotating mechanism for rotating a pair of grasping forceps about the longitudinal axis of an elongated member each time the grasping forceps that are disposed on the distal end of the elongated member which is inserted in a body are to be opened or closed (see, for example, PTL 1—Japanese Patent Laid-Open No. 2005-237498). The rotating mechanism includes protrusions fixed to a wire that is reciprocably movable along the longitudinal-axis of the elongated member for opening and closing the grasping forceps. The protrusions are guided in circumferential directions by slanted surfaces of guide members that are fixed to the elongated member at respective positions that are spaced from each other in the longitudinal-axis directions of the elongated member, one on each side of the guide member interposed therebetween, for thereby rotating the grasping forceps fixed to the distal end of the wire.

However, the rotating mechanism disclosed in PTL 1 is disadvantageous in that it is unable to rotate the grasping forceps on the distal end unless they are opened or closed, and if the grasping forces are rotated when they are disposed in the vicinity of a tissue, they may continue to rotate while their graspers are pinching the tissue by mistake.

Furthermore, the disclosed rotating mechanism is also disadvantageous in that since the movement of the wire along the longitudinal axis for opening and closing the grasping forceps is limited by the engagement between the protrusions and the guide members for rotating the grasping forceps, sufficient grasping forces cannot be obtained.

BRIEF SUMMARY OF EMBODIMENTS

The disclosed technology has been made under the above circumstances. It is an object of the disclosed technology to provide a rotating mechanism for treatment tools that is capable of rotating a treatment portion on the distal end of an elongated member about the longitudinal axis of the elongated member without operating the treatment portion.

According to an aspect of the disclosed technology, there is provided a rotating mechanism for a treatment tool, including a rotating member supported on a distal end of an elongated member for rotation about the longitudinal axis of the elongated member, the treatment tool being fixed to the rotating member, an axial force transmitting member disposed along the elongated member, for transmitting axial forces, an actuating member fixed to a distal end of the axial force transmitting member and mounted on the elongated member for rotation about the longitudinal axis and movement along the longitudinal axis, and a converting mechanism for converting linear movement of the actuating member along the longitudinal axis due to an axial force transmitted by the axial force transmitting member to rotary movement about the longitudinal axis, in which the actuating member and the rotating member are combined with each other such that the actuating member and the rotating member are movable relatively to each other along the longitudinal axis and nonrotatable relatively to each other about the longitudinal axis.

According to the present aspect, when a tractive force is applied to the proximal end of the axial force transmitting member, an axial force is transmitted through the axial force transmitting member to its distal end, moving the actuating member fixed to the distal end of the axial force transmitting member linearly along the longitudinal axis of the elongated member. The linear movement of the actuating member is converted by the converting mechanism to rotary movement of the actuating member about the longitudinal axis.

Since the actuating member and the rotating member are combined with each other such that they are movable relatively to each other along the longitudinal axis, the rotating member does not move along the longitudinal axis even when the actuating member moves along the longitudinal axis. On the other hand, since the actuating member and the rotating member are combined with each other such that they are not movable relatively to each other about the longitudinal axis, the rotating member also rotates as the actuating member rotates about the longitudinal axis.

The treatment tool attached to the rotating member can thus be rotated about the longitudinal axis at the distal end of the elongated member. In other words, the tractive force applied to the proximal end of the axial force transmitting member causes the treatment tool disposed on the distal end of the elongated member to rotate about the longitudinal axis of the elongated member without operating the treatment tool.

In the above aspect, the converting mechanism may have a protrusion attached to either one of the actuating member and the elongated member and projecting radially therefrom, and a guide portion fixed to the other of the actuating member and the elongated member on at least one side of the protrusion along the longitudinal axis, and the guide portion may have a slanted surface that is slanted in a direction along the longitudinal axis along a circumferential direction about the longitudinal axis, for guiding the protrusion in contact therewith.

With this arrangement, when a tractive force is applied to the axial force transmitting member, moving the protrusion toward a proximal-end side along the longitudinal axis, the protrusion is brought into contact with the slanted surface that is attached to the elongated member on one side along the longitudinal axis and moved along the slanted surface, so that the converting mechanism converts the linear movement of the protrusion along the longitudinal axis into rotary movement about the longitudinal axis.

In the above aspect, the guide portion may include a pair of guide portions disposed one on each side of the protrusion along the longitudinal axis and spaced from each other in facing relationship, one of the guide portions may have an array of slanted surfaces that are slanted in one direction and arrayed at a predetermined pitch, and the other of the guide portions may have an array of slanted surfaces that are slanted in an opposite direction to the slanted surfaces of the one of the guide portions and arrayed out of phase with the slanted surfaces of the one of the guide portions in the circumferential direction.

With this arrangement, when the projection moves in one direction along the longitudinal axis, the protrusion is brought into contact with either one of the slanted surfaces of the one of the guide portions and moved so as to slide on the slanted surface, whereupon the protrusion is rotated in one direction about the longitudinal axis. Thereafter, when the protrusion is moved in another direction along the longitudinal axis, the protrusion is brought into contact with either one of the slanted surfaces of the other of the guide portions and moved so as to slide on the slanted surface, whereupon the protrusion is rotated about the longitudinal axis.

In this case, as the protrusion contacts the slanted surfaces of the guide portions that are slanted in the opposite directions when the protrusion moves in different directions along the longitudinal axis, the protrusion is continuously moved in one direction about the longitudinal axis simply when the protrusion is repeatedly reciprocably moved along the longitudinal axis. The protrusion attached to the axial force transmitting member and the actuating member can thus easily be rotated about the longitudinal axis, continuously rotating the rotating member that engages the actuating member and the treatment tool about the longitudinal axis.

In the above aspect, the guide portion may include a pair of guide portions disposed one on each side of the protrusion along the longitudinal axis and spaced from each other in facing relationship, one of the guide portions may have an array of slanted surfaces that are slanted in both directions along the longitudinal directions along the circumferential direction and alternately arrayed at a predetermined pitch, and the other of the guide portions may have a first guide portion having an array of slanted surfaces that are slanted in one direction along the longitudinal axis along the circumferential direction and that are arrayed at a predetermined pitch, and a second guide portion having an array of slanted surfaces that are slanted in another direction along the longitudinal axis along the circumferential direction and that are arrayed at a predetermined pitch, the first guide portion and the second guide portion being replaceable with each other.

With this arrangement, when the projection moves in one direction along the longitudinal axis, the protrusion is brought into contact with either one of the slanted surfaces of the one of the guide portions and moved so as to slide on the slanted surface, whereupon the protrusion is rotated in one direction about the longitudinal axis. Thereafter, when the protrusion is moved in another direction along the longitudinal axis, the protrusion is brought into contact with either one of the slanted surfaces of the other of the guide portions and moved so as to slide on the slanted surface, whereupon the protrusion is rotated about the longitudinal axis.

In this case, by setting either one of the first guide portion and the second guide portion as the other guide portion, the protrusion can continuously be rotated in one direction about the longitudinal axis depending on the direction of the slanted surfaces of the first guide portion or the second guide portion that is set as the other guide portion. The direction of rotation of the treatment tool can thus be changed as desired.

In the above aspect, one of the guide portions that is disposed on a proximal-end side along the longitudinal axis may have a slot defined at a proximal end of each of the slanted surfaces, the slot having a width large enough to accommodate the protrusion therein and extending along the longitudinal axis.

With this arrangement, while the protrusion is being accommodated in the slot, even if an external force is applied tending to rotate the treatment tool about the longitudinal axis, the protrusion circumferentially abuts against a slot wall, thereby holding the treatment tool against rotation with respect to the elongated member.

In the above aspect, one of the actuating member and the rotating member may have a recess extending along the longitudinal axis and having a constant non-circular cross-sectional shape, and the other of the actuating member and the rotating member may have a projection that can be fitted in the recess along the longitudinal axis, the projection having a cross-sectional shape that is complementary to the recess.

With this arrangement, as the recess having the non-circular cross-sectional shape and the projection having the cross-sectional shape complementary to the recess are inter-fitted, the actuating and the rotating member can easily be coupled to each other such that they are movable relatively to each other along the longitudinal axis and nonrotatable relatively to each other about the longitudinal axis.

In the above aspect, the elongate member and the axial force transmitting member may be made of flexible material.

With this arrangement, the elongate member and the axial force transmitting member may be bendably inserted into a passage such as a tortuous body cavity or the like. When a tractive force is then applied to the axial force transmitting member at the proximal end of the elongate member, the treatment tool on the distal end of the elongate member can be rotated about the longitudinal axis.

In the above aspect, the elongate member, the axial force transmitting member, the actuating member, and the rotating member may have respective through holes defined axially therethrough.

With this arrangement, the axial force transmitting member for actuating the treating tool may be led from the proximal end of the elongate member through the through holes to the treatment tool. The treatment tool can thus be rotated and operated independently.

The disclosed technology offers the advantage that a rotating mechanism is capable of rotating a treatment portion on the distal end of an elongate member about the longitudinal axis of the elongate member without operating the treatment portion.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 7 is a transverse cross-sectional view illustrating protrusions on the actuating member of the rotating mechanism for a treatment tool illustrated in FIG. 1.

FIG. 8 is a development view illustrating the operation trajectory of the protrusions with respect to guide portions in the converting mechanism of FIG. 6.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

A rotating mechanism 1 for treatment tools according to an embodiment of the disclosed technology will hereinafter be described with reference to the drawings.

The rotating mechanism 1 for a treatment tool according to the present embodiment is a mechanism for rotating a treatment portion or treatment tool such as a pair of grasping forceps 3 or the like mounted on the distal end of an elongated member 2 of a tubular shape such as a flexible sheath, about the longitudinal axis of the elongated member 2 with a manipulation at the proximal end of the elongated member 2. The rotating mechanism 1, the elongated member 2, and the treatment portion 3 forms a treatment device as a whole.

Figure 1:
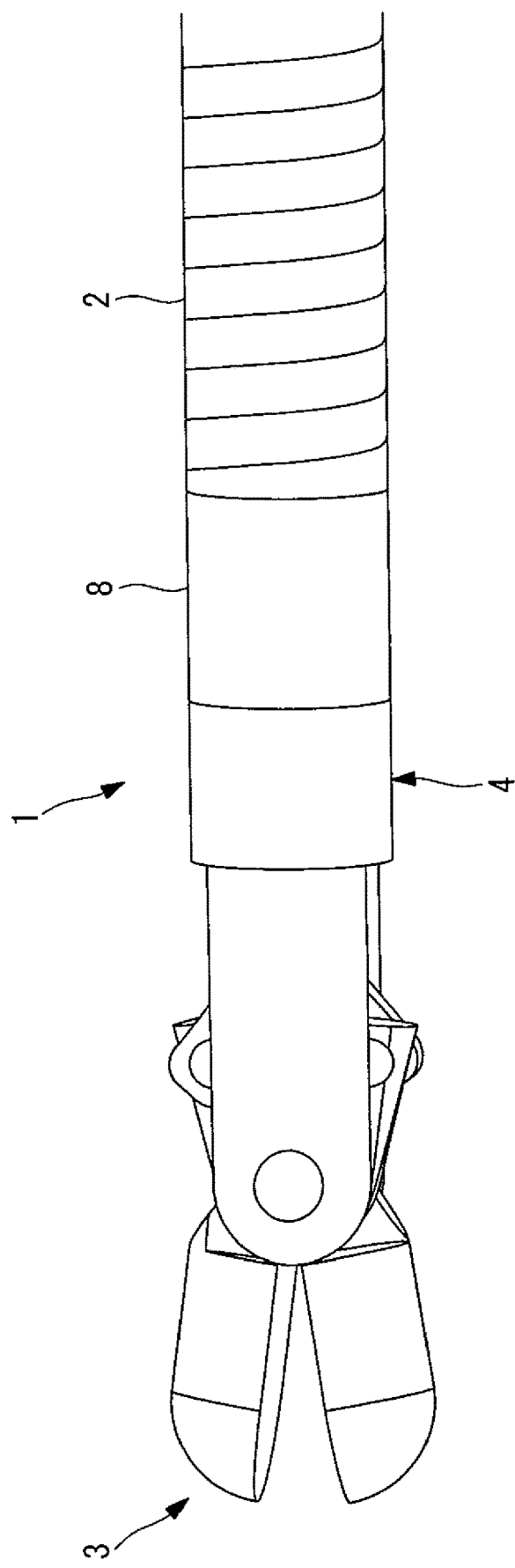
FIG. 1 is a partial side elevational view illustrating a treatment tool including a rotating mechanism therefor according to an embodiment of the disclosed technology.
Figure 2:
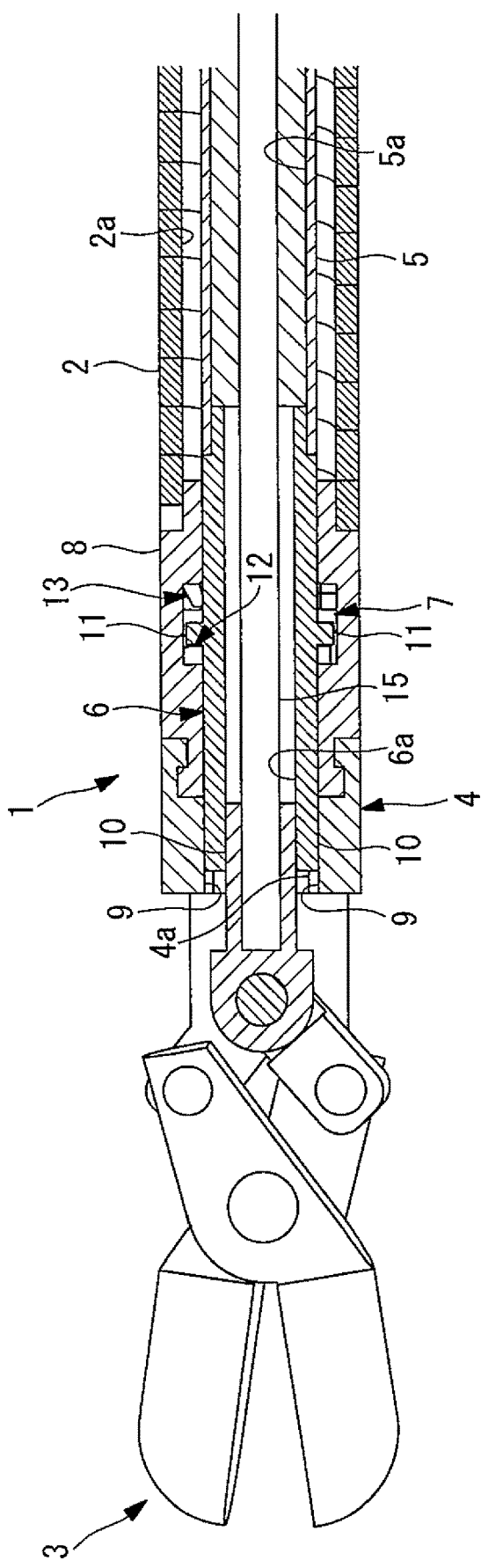
FIG. 2 is a longitudinal cross-sectional view of the rotating mechanism illustrated in FIG. 1.

As illustrated in FIGS. 1 and 2, the rotating mechanism 1 for a treatment tool according to the present embodiment includes a rotary member 4 supported on the distal end of the elongated member 2 for rotation about the longitudinal axis thereof. The rotating mechanism 1 for a treatment tool also includes a flexible tubular axial force transmitting member 5 extending through a central through hole 2a defined in the longitudinal member 2 over the full length of the longitudinal member 2, for transmitting axial forces. The rotating mechanism 1 for a treatment tool also includes an actuating member 6 attached to the distal end of the axial force transmitting member 5 and supported thereon for linear movement along the longitudinal axis and rotation about the longitudinal axis. The rotating mechanism 1 for a treatment tool also includes a converting mechanism 7 for converting part of the linear movement of the actuating member 6 along the longitudinal axis into rotary movement about the longitudinal axis.

The elongated member 2 includes a hollow cylindrical member 8. The hollow cylindrical member 8 is attached to the distal end of the elongated member 2 coaxially therewith. The rotating member 4 is of a hollow cylindrical shape coaxial with the elongated member 2 and attached to the distal end of the elongated member 2 for rotation about the longitudinal axis thereof.

The actuating member 6 is also a hollow cylindrical member having a through hole 6a defined therein that extends along the longitudinal axis, and has a proximal end attached to the axial force transmitting member 5.

As illustrated in FIG. 1, the pair of grasping forceps 3 are attached to the rotating member 4. When the rotating member 4 is rotated about the longitudinal axis, the grasping forceps 3 are also rotated about the longitudinal axis in unison with the rotating member 4.

Figure 3:
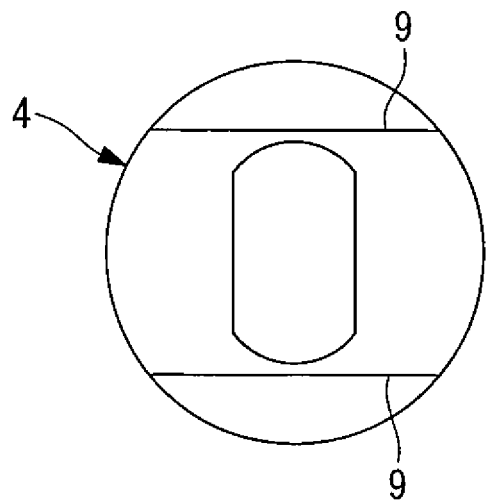
FIG. 3 is a front elevational view illustrating a transverse shape of recesses defined in a rotating member of the rotating mechanism for a treatment tool illustrated in FIG. 1.

As illustrated in FIGS. 2 and 3, the rotating member 4 has a pair of recesses 9 defined therein that extend along the longitudinal axis and have a constant non-circular cross-sectional shape. In an example illustrated in FIG. 3, the cross-sectional shape of the recesses 9 is a shape formed as if by cutting away part of a circular shape with two parallel planes.

Figure 4:
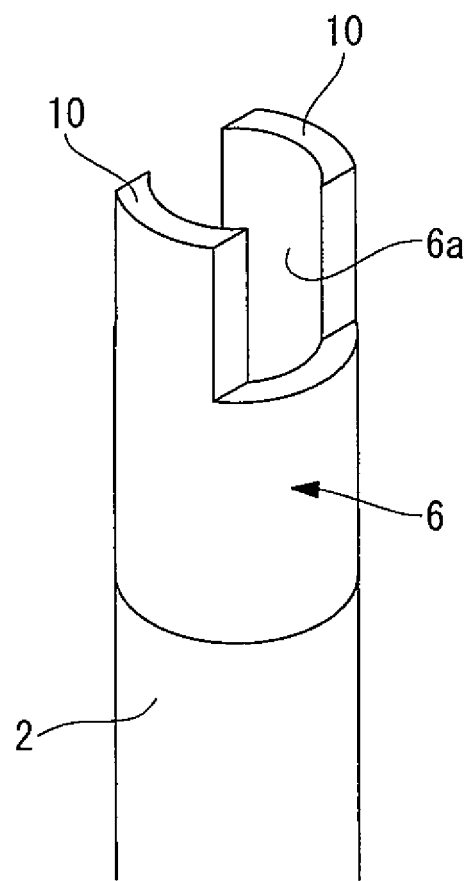
FIG. 4 is a perspective view illustrating projections on an actuating member of the rotating mechanism for a treatment tool illustrated in FIG. 1.
Figure 5:
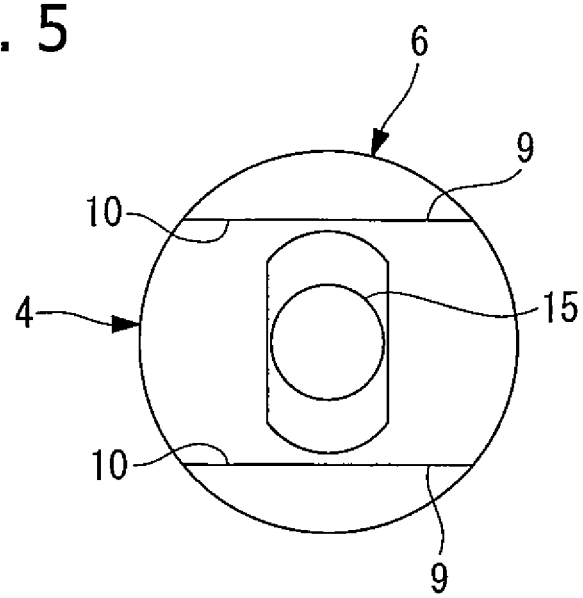
FIG. 5 is a plan view illustrating the manner in which the projections of FIG. 4 are fitted in the recesses of FIG. 3.

As illustrated in FIG. 4, the actuating member 6 has on its distal end a pair of projections 10 extending along the longitudinal axis. The projections 10 have a cross-sectional shape complementary to the recesses 9 of the rotating member 4 for being fitted in the recesses 9. In other words, the projections 10 also have a shape formed as if by cutting away circumferential part of a cylindrical surface with two parallel planes.

As illustrated in FIGS. 2 through 5, when the projections 10 are fitted in the recesses 9, the actuating member 6 is prevented from moving circumferentially about the longitudinal axis relatively to the rotating member 4 while being allowed to move along the longitudinally relatively to the rotating member 4.

Figure 6:
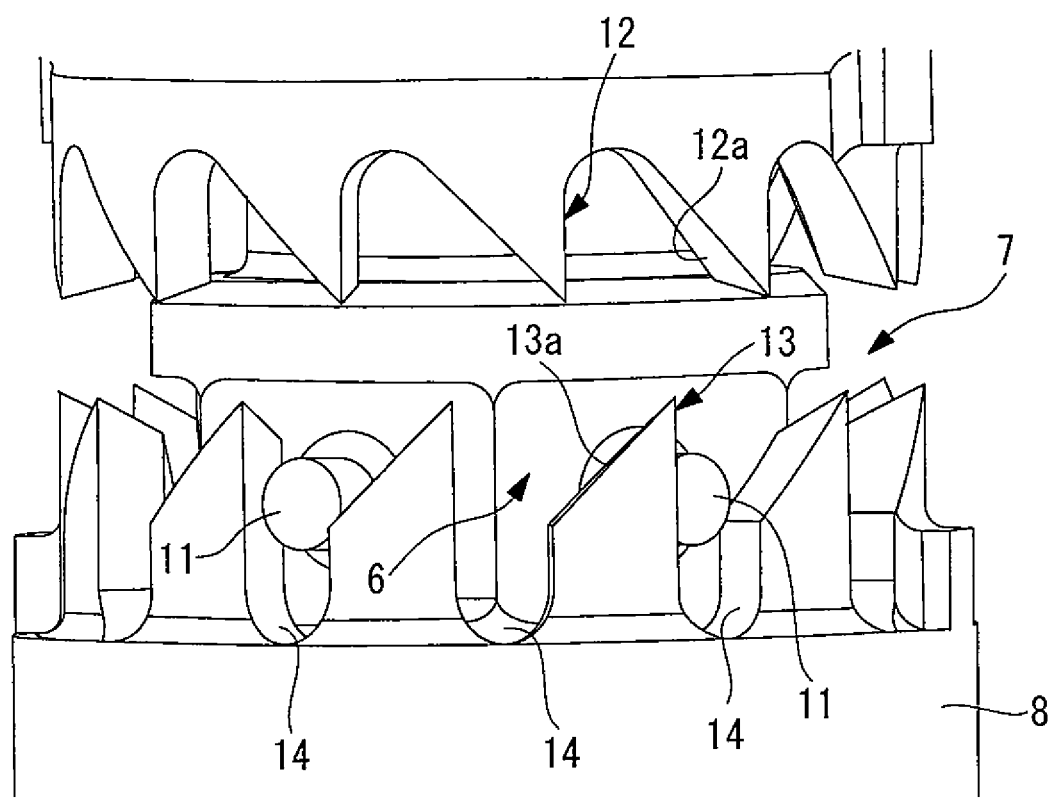
FIG. 6 is a partial side elevational view illustrating a converting mechanism of the rotating mechanism for a treatment tool illustrated in FIG. 1.

As illustrated in FIG. 2, the converting mechanism 7 includes one or more protrusions 11 protruding radially outwardly from circumferential part of the actuating member 6, and guide portions 12 and 13 defined in an inner surface of the hollow cylindrical member 8 on the distal end of the elongated member 2, as illustrated in FIG. 6. FIG. 6 is a view of the two guide portions 12 and 13 defined in the inner surface of the hollow cylindrical member 8 and the actuating member 6 disposed radially inwardly of the hollow cylindrical member 8, as viewed from radially outside the hollow cylindrical member 8. As illustrated in FIG. 7, the protrusions 11 are formed as six round columns disposed in a substantially central position along the longitudinal axis on the actuating member 6 and extending radially outwardly at equal intervals.

The guide portions 12 and 13 are disposed one on each side of the protrusions 11 along the longitudinal axis. Each of the guide portions 12 and 13 includes a circumferential array of twelve slanted surfaces 12a and 13a that are slanted in one direction along the longitudinal axis and arrayed at a constant pitch in the circumferential directions about the longitudinal axis. The guide portion 12 that is disposed on a distal-end side of the protrusions 11 and the guide portion 13 that is disposed on a proximal-end side of the protrusions 11 have respective slanted surfaces 12a and 13a that are slanted in opposite directions and that are angularly shifted out of phase by 30°.

Specifically, the guide portion 12 that is disposed on the distal-end side of the protrusions 11 is slanted to the proximal-end side along the longitudinal axis as viewed clockwise toward the distal-end side, whereas the guide portion 13 that is disposed on the proximal-end side of the protrusions 11 is slanted to the distal-end side along the longitudinal axis as viewed clockwise toward the distal-end side.

The guide portion 13 that is disposed on the proximal-end side of the protrusions 11 has slots 14 defined therein at the positions closest to the proximal-end side of the respective slanted surfaces 13a. The slots 14 have a width slightly larger than the outside diameter of the protrusions 11 and extend along the longitudinal axis.

As illustrated in FIG. 2, a wire 15 for actuating the grasping forceps 3 extends through a through hole 4a defined centrally through the rotating member 4, a through hole 6a in the actuating member 6, and a through hole 5a in the axial force transmitting member 5. The wire 15 has a distal end coupled to the grasping forceps 3 and a proximal end portion extending out of the proximal end of the elongated member 2. Tractive forces can be applied to the proximal end portion of the wire 15 manually or by an actuator.

Operation of the rotating mechanism 1 for treatment tools thus constructed according to the present embodiment will hereinafter be described.

When an axial force for pulling the axial force transmitting member 5 toward the proximal-end side is applied at the proximal end of the elongated member 2, the axial force transmitting member 5 is moved toward the proximal-end side along the longitudinal axis, and the actuating member 6 attached to the distal end of the axial force transmitting member 5 is also moved linearly toward the proximal-end side along the longitudinal axis.

FIG. 8 is a development view illustrating the operation trajectory of the protrusions 11 with respect to the guide portions 12 and 13 at the time the axial force transmitting member 5 is reciprocably moved along the longitudinal axis.

When the actuating member 6, i.e., the protrusion 11, is moved linearly from a position A in FIG. 8 along the longitudinal axis toward the proximal-end side, the protrusion 11 is brought into contact at a position B with one of the slanted surfaces 13a of the guide portion 13 that is disposed closer to the proximal-end side than the protrusion 11, and then is guided so as to slide on the slanted surface 13a. As a result, the converting mechanism 7 converts part of the linear movement of the protrusion 11 into rotary movement around the longitudinal axis. Therefore, the actuating member 6 is rotated in the direction indicated by the arrow P about the longitudinal axis while moving along the longitudinal axis toward the proximal-end side.

The projections 10 on the distal end of the actuating member 6 are fitted into the recesses 9 of the rotating member 4. Since the cross-sectional shapes of the projections 10 and the recesses 9 are non-circular, the movement of the actuating member 6 along the longitudinal axis is not transmitted to the rotating member 4, but they are moved relatively to each other along the longitudinal axis, and the rotation of the actuating member 6 about the longitudinal axis is transmitted to the rotating member 4, which is rotated about the longitudinal axis.

As the grasping forceps 3 are attached to the rotating member 4, the grasping forceps 3 are rotated in unison with the rotating member 4.

When an axial force tending to press the axial force transmitting member 5 toward the distal-end side is applied to the proximal end of the elongated member 2 with the protrusion 11 in a position C, the axial force transmitting member 5 is moved along the longitudinal axis toward the distal-end side, and the actuating member 6 attached to the distal end of the axial force transmitting member 5 is also moved linearly toward the proximal-end side along the longitudinal axis.

When the actuating member 6 is moved linearly along the longitudinal axis, the protrusion 11 is brought into contact at a position D with one of the slanted surfaces 12a of the other guide portion 12 that is disposed closer to the distal-end side than the protrusion 11, and then is guided so as to slide on the slanted surface 12a. As a result, the converting mechanism 7 converts part of the linear movement of the protrusion 11 into rotary movement around the longitudinal axis. Therefore, the actuating member 6 is rotated about the longitudinal axis while moving along the longitudinal axis toward the distal-end side.

In this case, too, since the projections 10 of the actuating member 6 and the recesses 9 of the rotating member 4 are interfitted, the movement of the actuating member 6 along the longitudinal axis is not transmitted to the rotating member 4, but they are moved relatively to each other along the longitudinal axis, and the rotation of the actuating member 6 about the longitudinal axis is transmitted to the rotating member 4, which is rotated about the longitudinal axis in the direction indicated by the arrow P.

In other words, the protrusion 11 is moved with respect to the two guide portions 12 and 13, as illustrated in FIG. 8. The grasping forceps 3 are rotated in one direction about the longitudinal axis of the elongated member 2 simply when the axial force transmitting member 5 is reciprocably moved along the longitudinal axis.

With the rotating mechanism 1 for treatment tools according to the present embodiment, the grasping forceps 3 on the distal end of the elongated member 2 can thus be rotated about the longitudinal axis by a simple process of reciprocally moving the axial force transmitting member 5 at the proximal end of the elongated member 2. The wire 15 for opening and closing the grasping forceps 3 extends through the central through holes 2a, 4a and 6a in the elongated member 2, the actuating member 6, and the rotating member 4 and is connected to the grasping forceps 3. Therefore, the grasping forceps 3 can be opened and closed independently of the rotation of the grasping forceps 3.

Specifically, when the grasping forceps 3 are rotated about the longitudinal axis, the grasping forceps 3 do not need to be opened and closed. Consequently, when the grasping forceps 3 are rotated, they are prevented from being opened and closed and causing problems such as pinching a peripheral tissue.

As the operation to open and close the grasping forceps 3 is not limited by the operation to rotate the grasping forceps 3, the tractive force applied to the wire 15 is directly used to open and close the grasping forceps 3, resulting in an advantage in that the grasping forceps 3 can grasp an object to be grasped with a strong force.

According to the present embodiment, moreover, the guide portion 13 that is disposed closer to the proximal-end side than the protrusion 11 has the slots 14 that extend along the longitudinal axis for accommodating the protrusion therein. When the axial force transmitting member 5 is continuously pulled toward the proximal-end side, the protrusion 11 guided by one of the slanted surfaces 13a to move into the corresponding slot 14, as indicated by C in FIG. 8. As the protrusion 11 is circumferentially enclosed by the inner wall surface of the slot 14, the protrusion 11 is locked against rotation with respect to the elongated member 2 even when an external force tending to rotate the protrusion 11 about the longitudinal axis is applied. In other words, as the protrusion 11 is accommodated in the slot 14 while the object to be grasped is being grasped by the grasping forceps 3, the grasping forceps 3 that is grasping the object to be grasped can easily be rotated about the longitudinal axis by a torsional torque applied to the elongated member 2.

Furthermore, the rotating mechanism 1 for treatment tools according to the present embodiment includes the six protrusions 11 spaced at equal intervals in the circumferential directions and the twelve slanted surfaces 12*a* and 13*a* of each of the guide portions 12 and 13. Therefore, the protrusions 11 are guided by every other slanted surfaces 12*a* and 13*a* such that the grasping forceps 3 can be rotated 30° about the longitudinal axis by a single act of reciprocating movement of the axial force transmitting member 5. However, the number of the protrusions 11 and the numbers of the slanted surfaces 12*a* and 13*a* are optional. In the present embodiment, the slanted surfaces 12*a* and 13*a* are slanted in such directions that the actuating member 6 is rotated counterclockwise as viewed toward the distal-end side when the protrusion 11 is reciprocally moved along the longitudinal axis. However, the slanted surfaces 12*a* and 13*a* may be slanted conversely.

In the present embodiment, moreover, the protrusions 11 protrude radially outwardly from the outer surface of the actuating member 6, and the guide portions 12 and 13 having the slanted surfaces 12*a* and 13*a* for contact with the protrusions 11 are defined in the inner surface of the hollow cylindrical member 8 formed in the elongated member 2. However, the protrusions 11 and the guide portions 12 and 13 may be disposed conversely. Specifically, the guide portions 12 and 13 may be defined on the outer surface of the actuating member 6, and the protrusions 11 may project radially inwardly from the inner surface of the hollow cylindrical member 8.

Figure 9:
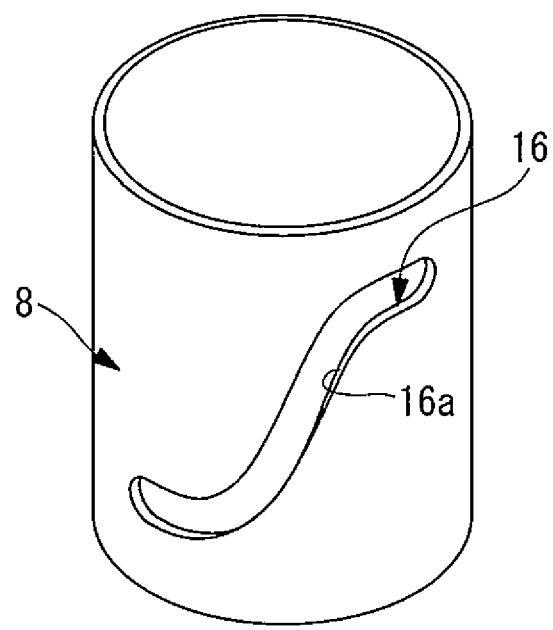
FIG. 9 is a side elevational illustrating a modification of the guide portions in the converting mechanism of FIG. 6.

The guide portions 12 and 13 are arranged such that the slanted surfaces 12*a* and 13*a* are arrayed thereon at a constant pitch. However, as illustrated in FIG. 9, the guide portions 12 and 13 may be replaced with a cam groove 16 for accommodating a protrusion 11 therein. The cam groove 16 may have a slanted surface 16*a* with a varying angle of tilt.

The guide portions 12 and 13 extend fully circumferentially around the hollow cylindrical member 8. If the guide portions 12 and 13 are replaced with the cam groove 16, then the cam groove 16 may extend partly circumferentially around the hollow cylindrical member 8.

The cam groove 16 allows the grasping forceps 3 to rotate in a selected direction by moving the axial force transmitting member 5 in either of the directions along the longitudinal axis.

In the present embodiment, the recesses 9 have a cross-sectional shape formed as if by cutting away part of a circular shape with planes, and the projections 10 have a cross-sectional shape complementary to the recesses 9. Instead, the recesses 9 and the projections 10 may have any of other optional non-circular cross-sectional shapes.

The grasping forceps 3 have been illustrated as the treatment portion. However, any of other optional treatment portions may be employed.

A treatment portion with joints may be employed, and the joints may be actuated by the wire 15 that are led through the central through holes 2*a*, 4*a* and 6*a* in the elongated member 2, the actuating member 6, and the rotating member 4.

Figure 10:
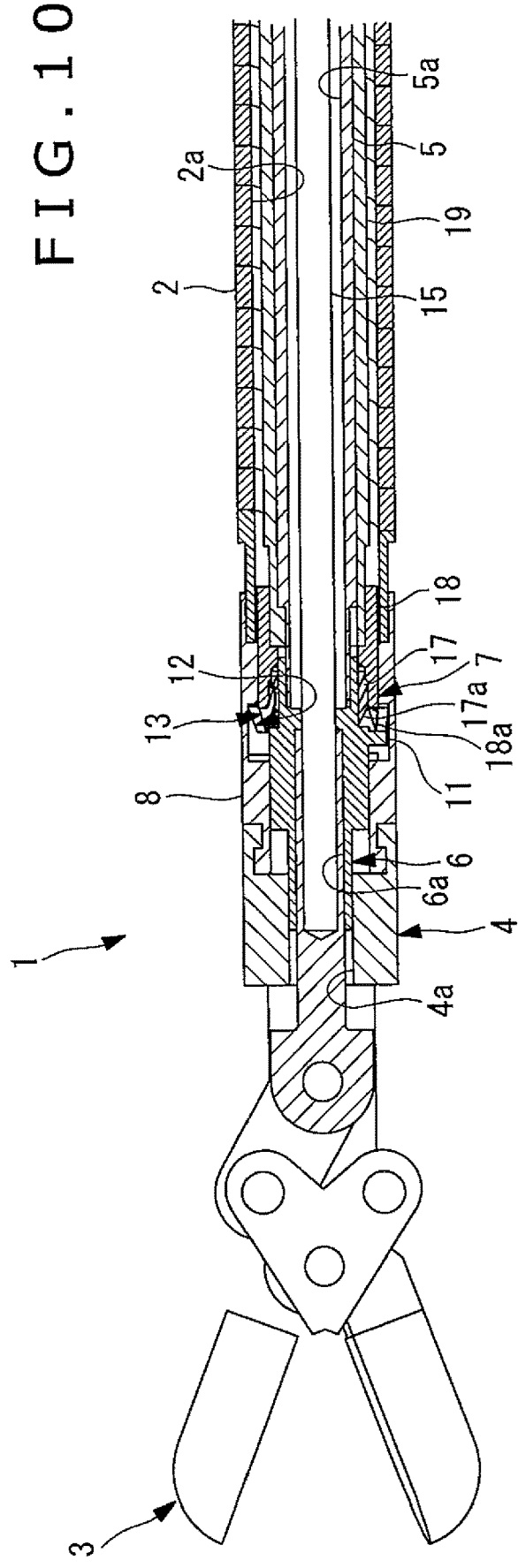
FIG. 10 is a longitudinal cross-sectional view illustrating a modification of the rotating mechanism for a treatment tool of FIG. 2.

The hollow cylindrical member 8 formed in the elongated member 2 includes the guide members 12, 13 that are disposed one on each side of the protrusions 11 along the longitudinal axis. Instead, as illustrated in FIG. 10, the guide portion 12 that is disposed on the distal-end side of the protrusions 11 may have an array of circumferentially alternate slanted surfaces 12*a* that are slanted in opposite directions, and the guide portion 13 that is disposed on the proximal-end side of the protrusions 11 may be provided on the hollow cylindrical member 8 formed in the elongated member 2. The rotating mechanism may include a first guide portion 17 having a circumferential array of slanted surfaces 17*a* that are slanted in one direction along the longitudinal axis and arrayed at a predetermined pitch in the circumferential directions about the longitudinal axis, a second guide portion 18 having a circumferential array of slanted surfaces 18*a* that are slanted in another direction along the longitudinal axis and arrayed at a predetermined pitch in the circumferential directions about the longitudinal axis, and another tubular axial force transmitting member 19 for moving the second guide portion 18 along the longitudinal axis.

Figure 11:
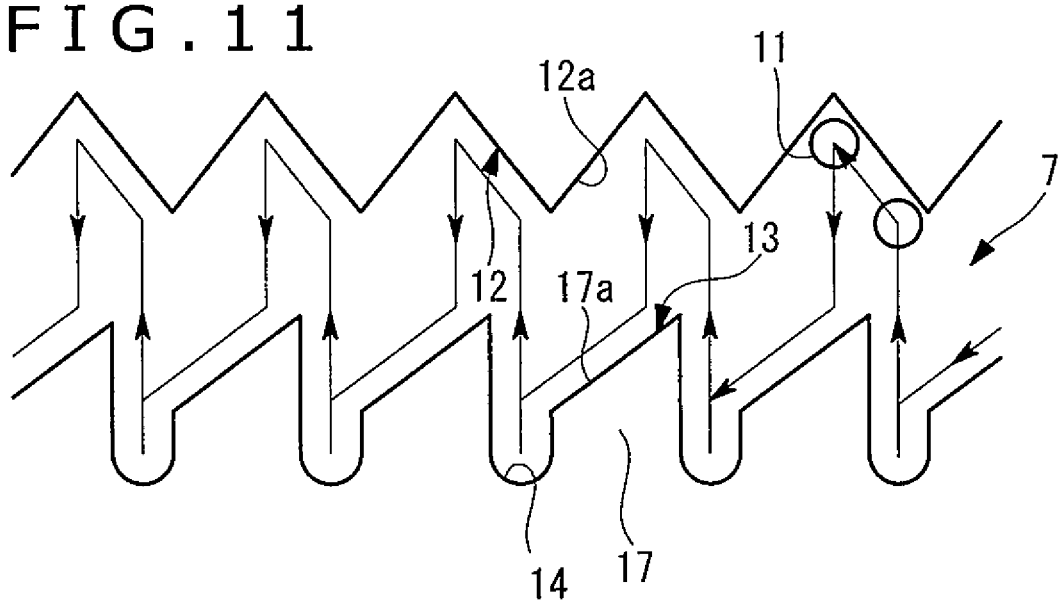
FIG. 11 is a development view illustrating one pattern of the operation trajectory of the protrusions with respect to the guide portions in the rotating mechanism for a treatment tool of FIG. 10.
Figure 12:
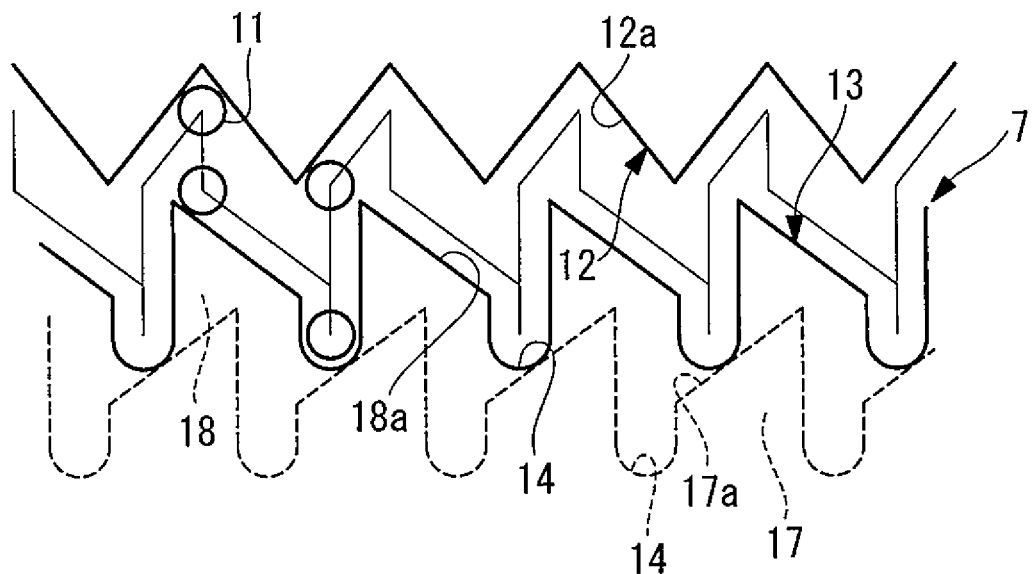
FIG. 12 is a development view illustrating another pattern of the operation trajectory of the protrusions with respect to the guide portions in the rotating mechanism for a treatment tool of FIG. 10.

In case the first guide portion 17 is disposed in a position close to the projections 11, as illustrated in FIG. 11, the projections 11 can continuously be moved in one direction when the axial force transmitting member 5 is reciprocably moved along the longitudinal axis. Conversely, in case the second guide portion 18 is disposed in a position close to the projections 11, as illustrated in FIG. 12, the projections 11 can continuously be moved in another direction when the axial force transmitting member 19 is reciprocably moved along the longitudinal axis. In other words, when the other axial force transmitting member 19 is moved along the longitudinal axis, the second guide member 18 is moved back and forth along the longitudinal axis, changing the direction in which the actuating member 6, i.e., the grasping forceps 3, is rotated depending on the relative positional relationship with the first guide member 17.

One aspect of the disclosed technology is directed to a rotating mechanism for a treatment tool or grasping forceps which comprises a rotating member having respective first and second ends. The first end is supported on a distal end of an elongated member for rotation about a longitudinal axis of the elongated member. The treatment tool or the grasping forceps is attached to the second end of the rotating member. An axial force transmitting member is configured to be disposed along the elongated member for transmitting axial forces. An actuating member is attached to a distal end of the axial force transmitting member and wherein both the actuating member and the axial force transmitting member are concentrically mounted inside the elongated member for rotary movement about the longitudinal axis and linear movement along the longitudinal axis. A converting mechanism is used for converting the linear movement to the rotary movement of the actuating member along the longitudinal axis due to an axial force transmitted by the axial force transmitting member. The linear movement of the actuating member along the longitudinal axis is not transmitted to the rotating member and the rotary movement of the actuating member about the longitudinal axis is transmitted to the rotating member.

The converting mechanism has a protrusion attached to either the actuating member or the elongated member and projecting radially therefrom. A guide portion attached opposite from the protrusion to either the actuating member or the elongated member on at least one side of the protrusion along the longitudinal axis. The guide portion has a slanted surface that is slanted to the longitudinal axis along a circumferential direction about the longitudinal axis for guiding the protrusion in contact therewith. The guide portion is defined by a pair of guide portions disposed one on each side of the protrusion along the longitudinal axis and spaced apart from one another in facing relationship. One of the pair of guide portions has an array of slanted surfaces that are slanted in one direction and arrayed at a predetermined pitch. The other one of the pair of guide portions has an array of slanted surfaces that are slanted in an opposite direction to the slanted surfaces of the one of the guide portions and arrayed out of phase with the slanted surfaces of the one of the guide portions in the circumferential direction. The guide portion is defined by three guide portions, namely, a first guide portion has an array of slanted surfaces that are slanted in both directions along respective the longitudinal and circumferential directions and alternately arrayed at a predetermined pitch, a second guide portion has an array of slanted surfaces that are slanted in one direction along the respective longitudinal and circumferential and that are arrayed at a predetermined pitch, and a third guide portion has an array of slanted surfaces that are slanted in different direction from the second guide portion along respective the longitudinal and circumferential direction and that are arrayed at a predetermined pitch. The first guide portion and the second guide portion are disposed on each side of protrusion along the longitudinal axis and spaced apart from one another in facing relationship. The third guide portion is disposed on the same side of the second guide portion coaxially. The second guide portion and the third guide portion are replaceable with each other. The converting mechanism converts the linear movement to the rotary movement in a first direction when the first guide portion is disposed more closely to the second guide portion than the third guide portion. The converting mechanism converts the linear movement to the rotary movement in a second direction opposite to the first direction when the first guide portion is disposed more closely to the third guide portion than the second guide portion. One of the guide portions that is disposed closer to a proximal-end side along the longitudinal axis has a slot defined at a proximal end of each of the slanted surfaces. The slot having a width large enough to accommodate the protrusion therein and to extend along the longitudinal axis. One of the actuating member and the rotating member has a recess extending along the longitudinal axis and having a constant non-circular cross-sectional shape, and the other of the actuating member and the rotating member has a projection fitted in the recess along the longitudinal axis, the projection having a cross-sectional shape that is complementary to the recess. The elongated member and the axial force transmitting member are made of flexible material. The elongated member, the axial force transmitting member, the actuating member, and the rotating member all of which have respective through holes that are defined axially therethrough.

Another aspect of the disclosed technology is directed to a treatment device that comprises an elongated member having a distal end and a proximal end. An axial force transmitting member includes a distal end and a proximal end. The axial force transmitting member is concentrically disposed inside the elongated member along the longitudinal axis. The axial force transmitting member is configured to transmit axial forces. The axial force transmitting member is configured to move along the longitudinal axis. An actuating member is attached to the distal end of the axial force transmitting member. The actuating member is engaged with an inner surface of the elongated member. The actuating member is configured to move along the longitudinal axis and is configured to be rotated about the longitudinal axis based on the axial forces transmitted by the axial force transmitting member. A rotating member is supported on the distal end of the elongated member and is configured to be rotated with the actuating member about a longitudinal axis of the elongated member. The rotating member is attached to the actuating member such that the actuating member and the rotating member are linearly movable relatively to one another along the longitudinal axis and nonrotatable relatively to one another about the longitudinal axis. A treatment tool is attached to the rotating member and is configured to be rotated with the rotating member about the longitudinal axis.

The actuating member has a protrusion projecting radially therefrom. The elongated member has a guide portion formed on the inner surface. The guide portion has a slanted surface for guiding the protrusion in contact therewith. The elongated member has a protrusion formed on the inner surface and projecting radially therefrom. The actuating member has a guide portion. The guide portion has a slanted surface for guiding the protrusion in contact therewith. The guide portion comprises a first guide portion and a second portion spaced apart one another. The first guide portion has a first array of slanted surfaces arrayed at a predetermined pitch in the circumferential direction. The second guide portion has a second array of slanted surfaces arrayed out of phase with the first array of slanted surfaces in the circumferential direction. The guide portion comprises a first guide portion and a second portion spaced apart one another. The first guide portion has a first array of slanted surfaces arrayed at a predetermined pitch in the circumferential direction. The second guide portion has a second array of slanted surfaces arrayed out of phase with the first array of slanted surfaces in the circumferential direction.

The first guide portion is disposed closer to the distal end of the axial force transmitting member than the second guide portion. The first guide portion has a slot defined at a proximal end of each of the slanted surfaces. The slot having a width large enough to accommodate the protrusion therein and extending along the longitudinal axis. The actuating member has a recess extending along the longitudinal axis and having a constant non-circular cross-sectional shape. The rotating member has a projection that is to be fitted in the recess along the longitudinal axis. The projection having a cross-sectional shape that is complementary to the recess. The rotating member has a recess extending along the longitudinal axis and having a constant non-circular cross-sectional shape. The actuating member has a projection that is to be fitted in the recess along the longitudinal axis. The projection having a cross-sectional shape that is complementary to the recess. The axial force transmitting member is configured to move reciprocably along the longitudinal axis so that the treatment tool is configured to be rotated in one direction about the longitudinal axis.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless other-wise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more", "at least", "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

NUMERAL REFERENCE LIST

1 Rotating mechanism for treatment tools
2 Elongated member
2a, 4a, 6a Through hole
3 Grasping forceps or treatment tool
4 Rotating member
5 Axial force transmitting member
6 Actuating member
7 Converting mechanism
9 Recess
10 Projection
11 Protrusion
12, 13 Guide portion
12a, 13a, 16a, 17a, 18a Slanted surface
14 Slot
17 First guide portion
18 Second guide portion

What is claimed is:

1. A rotating mechanism for a treatment tool or grasping forceps, comprising:
   a rotating member having respective first and second ends wherein the first end being supported on a distal end of an elongated member for rotation about a longitudinal axis of the elongated member, the treatment tool being attached to the second end of the rotating member;
   an axial force transmitting member configured to be disposed along the elongated member for transmitting axial forces;
   an actuating member being attached to a distal end of the axial force transmitting member and wherein both the actuating member and the axial force transmitting member being concentrically mounted inside the elongated member for rotary movement about the longitudinal axis and linear movement along the longitudinal axis; and
   a converting mechanism being used for converting the linear movement to the rotary movement of the actuating member along the longitudinal axis due to an axial force transmitted by the axial force transmitting member wherein
   the linear movement of the actuating member along the longitudinal axis is not transmitted to the rotating member and the rotary movement of the actuating member about the longitudinal axis is transmitted to the rotating member.

2. The rotating mechanism for a treatment tool of claim 1, wherein
   the converting mechanism has a protrusion attached to either the actuating member or the elongated member and projecting radially therefrom, and a guide portion attached opposite from the protrusion to either the actuating member or the elongated member on at least one side of the protrusion along the longitudinal axis; and
   the guide portion has a slanted surface that is slanted to the longitudinal axis along a circumferential direction about the longitudinal axis for guiding the protrusion in contact therewith.

3. The rotating mechanism for a treatment tool of claim 2, wherein
   the guide portion is defined by a pair of guide portions disposed one on each side of the protrusion along the longitudinal axis and spaced apart from one another in facing relationship;
   one of the pair of guide portions has an array of slanted surfaces that are slanted in one direction and arrayed at a predetermined pitch; and
   the other one of the pair of the guide portions has an array of slanted surfaces that are slanted in an opposite direction to the slanted surfaces of the one of the guide portions and arrayed out of phase with the slanted surfaces of the one of the guide portions in the circumferential direction.

4. The rotating mechanism for a treatment tool of claim 2, wherein
   the guide portion is defined by three guide portions;
   a first guide portion has an array of slanted surfaces that are slanted in both directions along respective the longitudinal and circumferential directions and alternately arrayed at a predetermined pitch;
   a second guide portion has an array of slanted surfaces that are slanted in one direction along the respective longitudinal and circumferential and that are arrayed at a predetermined pitch; and
   a third guide portion has an array of slanted surfaces that are slanted in different direction from the second guide portion along respective the longitudinal and circumferential direction and that are arrayed at a predetermined pitch wherein the first guide portion and the second guide portion disposed on each side of protrusion along the longitudinal axis and spaced apart from one another in facing relationship, the third guide portion disposed on the same side of the second guide portion coaxially, the second guide portion and the third guide portion being replaceable with each other.

5. The rotating mechanism for a treatment tool of claim 4, wherein the converting mechanism converts the linear movement to the rotary movement in a first direction when the first guide portion is disposed more closely to the second guide portion than the third guide portion, and the converting mechanism converts the linear movement to the rotary movement in a second direction opposite to the first direction when the first guide portion is disposed more closely to the third guide portion than the second guide portion.

6. The rotating mechanism for a treatment tool of claim 3, wherein one of the guide portions that is disposed closer to a proximal-end side along the longitudinal axis has a slot defined at a proximal end of each of the slanted surfaces, the slot having a width large enough to accommodate the protrusion therein and to extend along the longitudinal axis.

7. The rotating mechanism for a treatment tool of claim 1, wherein one of the actuating member and the rotating member has a recess extending along the longitudinal axis and having a constant non-circular cross-sectional shape, and the other of the actuating member and the rotating member has a projection fitted in the recess along the longitudinal axis, the projection having a cross-sectional shape that is complementary to the recess.

8. The rotating mechanism for a treatment tool of claim 1, wherein the elongated member and the axial force transmitting member are made of flexible material.

9. The rotating mechanism for a treatment tool of claim 1, wherein the elongated member, the axial force transmitting member, the actuating member, and the rotating member all of which have respective through holes that are defined axially therethrough.

10. A treatment device comprising:

an elongated member having a distal end and a proximal end;

an axial force transmitting member having a distal end and a proximal end, the axial force transmitting member concentrically disposed inside the elongated member along the longitudinal axis, the axial force transmitting member configured to transmit axial forces, the axial force transmitting member configured to move along the longitudinal axis;

an actuating member attached to the distal end of the axial force transmitting member, the actuating member engaged with an inner surface of the elongated member, the actuating member configured to move along the longitudinal axis and configured to be rotated about the longitudinal axis based on the axial forces transmitted by the axial force transmitting member;

a rotating member supported on the distal end of the elongated member and configured to be rotated with the actuating member about a longitudinal axis of the elongated member, the rotating member being attached to the actuating member such that the actuating member and the rotating member are linearly movable relatively to one another along the longitudinal axis and nonrotatable relatively to one another about the longitudinal axis; and a treatment tool being attached to the rotating member and configured to be rotated with the rotating member about the longitudinal axis.

11. The treatment device of claim 10, wherein the actuating member has a protrusion projecting radially therefrom, the elongated member has a guide portion formed on the inner surface, the guide portion has a slanted surface for guiding the protrusion in contact therewith.

12. The treatment device of claim 10, wherein the elongated member has a protrusion formed on the inner surface and projecting radially therefrom, the actuating member has a guide portion, the guide portion has a slanted surface for guiding the protrusion in contact therewith.

13. The treatment device of claim 11, wherein the guide portion comprises a first guide portion and a second portion spaced apart one another, the first guide portion has a first array of slanted surfaces arrayed at a predetermined pitch in the circumferential direction; and the second guide portion has a second array of slanted surfaces arrayed out of phase with the first array of slanted surfaces in the circumferential direction.

14. The treatment device of claim 12, wherein the guide portion comprises a first guide portion and a second portion spaced apart one another, the first guide portion has a first array of slanted surfaces arrayed at a predetermined pitch in the circumferential direction; and the second guide portion has a second array of slanted surfaces arrayed out of phase with the first array of slanted surfaces in the circumferential direction.

15. The treatment device of claim 14, wherein the first guide portion is disposed closer to the distal end of the axial force transmitting member than the second guide portion, and the first guide portion has a slot defined at a proximal end of each of the slanted surfaces, the slot having a width large enough to accommodate the protrusion therein and extending along the longitudinal axis.

16. The treatment device of claim 10, wherein the actuating member has a recess extending along the longitudinal axis and having a constant non-circular cross-sectional shape, and the rotating member has a projection that is to be fitted in the recess along the longitudinal axis, the projection having a cross-sectional shape that is complementary to the recess.

17. The treatment device of claim 10, wherein the rotating member has a recess extending along the longitudinal axis and having a constant non-circular cross-sectional shape, and the actuating member has a projection that is to be fitted in the recess along the longitudinal axis, the projection having a cross-sectional shape that is complementary to the recess.

18. The treatment device of claim 10, wherein the axial force transmitting member configured to move reciprocably along the longitudinal axis so that the treatment tool is configured to be rotated in one direction about the longitudinal axis.

* * * * *